United States Patent [19]

Jäger et al.

[11] 4,006,170

[45] Feb. 1, 1977

[54] PROCESS FOR THE PREPARATION OF 1-AMINOANTHRAQUINONE

[75] Inventors: Horst Jäger, Leverkusen; Erich Klauke, Odenthal, both of Germany

[73] Assignee: Bayer Aktiengesellschaft, Leverkusen, Germany

[22] Filed: June 17, 1975

[21] Appl. No.: 587,748

[30] Foreign Application Priority Data

June 29, 1974 Germany .......................... 2431409

[52] U.S. Cl. ............................. 260/378; 260/354; 260/397; 260/471 R
[51] Int. Cl.$^2$ .................. C07B 29/00; C07C 97/24
[58] Field of Search ............... 260/351, 378, 578 R

[56] References Cited

UNITED STATES PATENTS

| | | | |
|---|---|---|---|
| 1,916,216 | 7/1933 | Gubelmann et al. .............. | 260/351 |
| 2,174,118 | 9/1939 | Calcott et al. ..................... | 260/351 |
| 3,330,823 | 7/1967 | Bernstein et al. .......... | 260/518 R X |

FOREIGN PATENTS OR APPLICATIONS

| | | | |
|---|---|---|---|
| 2,352,067 | 10/1973 | Germany | |
| 373,129 | 5/1932 | United Kingdom ............... | 260/351 |

*Primary Examiner*—Allen B. Curtis
*Attorney, Agent, or Firm*—Burgess, Dinklage & Sprung

[57] ABSTRACT

A process for preparing 1-aminoanthraquinone, comprising the steps of:

a. reacting o-chloromethylphenylisocyanate with at least an equivalent amount of benzene in anhydrous hydrofluoric acid at a temperature of about −10° to 200° C to form the lactam of 2-amino-diphenylmethane-2'-carboxylic acid, b. saponifying the lactam of 2-amino-diphenylmethane-2'-carboxylic acid with aqueous alkali at a temperature above about 100° C to form the 2-amino-diphenylmethane-2'-carboxylic acid, c. contacting the 2-amino-diphenylmethane-2'-carboxylic acid with an acid condensation agent, thereby to convert the carboxylic acid to 4-amino-anthrone, and d. contacting the 4-aminoanthrone with an oxidizing agent in an acid or alkaline medium, thereby to convert the aminoanthrone to 1-aminoanthraquinone. Special conditions are also recited for carrying out the individual steps to obtain high yields.

24 Claims, No Drawings

PROCESS FOR THE PREPARATION OF 1-AMINOANTHRAQUINONE

The present invention relates to a process for the preparation of 1-aminoanthraquinone from o-chloromethylphenylisocyanate and benzene.

1-Aminoanthraquinone is usually prepared from anthraquinone-1-sulphonic acid by reaction with ammonia at about 175° C and 25–30 atmospheres gauge in the presence of an oxidizing agent (compare F.I.A.T. Report 1313, volume 2, page 59 and 60). Anthraquinone-1-sulphonic acid is obtained by sulphonation of anthraquinone with oleum in the presence of mercury or mercury compounds. The sulphonation only takes place incompletely and anthraquinone-1-sulphonic acid is obtained as a mixture with anthraquinone-2-sulphonic acid and anthraquinone-disulphonic acids, which necessitates a technically complicated isolation of the anthraquinone-1-sulphonic acid (compare Ullman, Enzyklopadie der Technischen Chemie (Encyclopaedia of Industrial Chemistry), 3rd edition, volume 3, page 667). Furthermore, mother liquors which contain mercury compounds, dilute sulphuric acid and inorganic salts are obtained from the sulphonation. The elimination of the mercury and the recovery of the sulphuric acid from mother liquors containing inorganic salts is only possible with considerable effort. The anthraquinone employed in the sulphonation is in general obtained by oxidation of anthracene, which in turn is to be found in coal tar. As a result of a shift in energy supply from coal to petroleum, the raw material for this process has become more scarce.

It is also possible to obtain 1-aminoanthraquinone from 1-nitroanthraquinone, the 1-nitroanthraquinone being obtained by nitration of anthraquinone with nitric acid, if appropriate in the presence of sulphuric acid, phosphoric acid, hydrofluoric acid and/or inert organic solvent (compare, for example, German Published Specification Nos. 2,233,185, 2,219,216, 2,204,516 2,252,013 and 2,103,360. The isolation of 1-nitroanthraquinone from other reaction products, the recovery of the acids employed and the raw material situation present the same problems as for the sulphonation of anthraquinone described above. Furthermore, only relatively unsatisfactory selectivites are achieved. For example, the conversion of 1-nitroanthraquinone to 1-aminoanthraquinone can be carried out with ammonia in solvents or with reducing agents in the presence of sulphuric acid (compare R. Oda, J. Soc. Chem. Ind., Japan, 43. Suppl. Binding 386 (1940), German Published Specification 2,211,411, and R. Oda and U. Ueda, Scientific Papers Inst. Phys. Chem. Research, Tokyo, 38, 44 (1940)). The isolation and purification of the 1-aminoanthraquinone thus obtainable entails additional effort.

There is therefore an interest in a process for the preparation of 1-aminoanthraquinone in which these disadvantages do not arise.

It is known that the lactam (I) of 1-amino-dipehnylmethane-2′-carboxylic acid can be obtained by condensation of 2-chloromethylphenylisocyanate with benzene in an inert solvent and in the presence of Friedel-Crafts catalysts (compare German Published Specification 2,352,067 and equation 1):

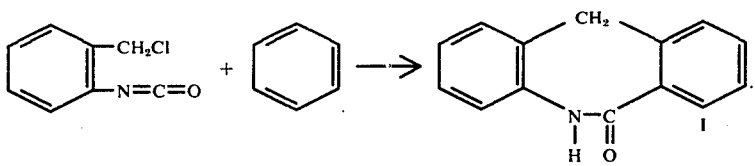

Equation 1

According to that process, a mixture of o-chloromethylphenylisocyanate and o-dichloromethylphenylisocyanate is reacted with an excess of anhydrous benzene in the presence of aluminum chloride as a Friedel-Crafts catalyst and only after very involved working up and purification is morphantridin-6-(5H)-one (= the lactam of 2-amino-diphenylmethane-2′-carboxylic acid), melting at 193°–196° C, obtained (compare Example 1b of German Published Specification 2,352,067). Because of the complicated nature of this process, it is only suitable for the preparaton of relatively small amounts of morphantridin-6-(5H)-one, such as are required, for example, for the preparation of pharmaceuticals, and is not suitable as a component step in the large-scale industrial preparation of 1-amino-anthraquinone which is required in quantities of several thousand tons per annum. Furthermore, although no data are available on the yield of the process, it is probably not particularly high, because the purification entails several stages, all of which will necessarily be associated with losses.

Furthermore it is known that the lactam (I) can be saponified to 2-amino-diphenylmethane-2′-carboxylic acid (II) by heating to 160° C in 10% strength methanolic potassium hydroxide solution for twelve hours (compare Liebig's Annalen der Chemie 594, 89 (1955) and equation 2):

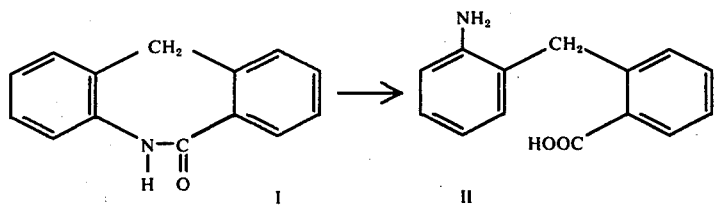

Equation 2

This saponification is followed by cautious neutralization of the mixture with dilute phosphoric acid, whereupon the free acid (II) separates out. This method is unsuitable for a large-scale industrial process since methanol has a considerable vapor pressure at 160° C, a large amount of methanol is required (about 12 parts of methanol per part of lactam) and the molar ratio of potassium hydroxide solution to lactam, namely 4.7 to 1, is unfavorable. Furthermore, the yield of 2-amino-diphenylmethane-2'-carboxylic acid is not known.

Finally, it is also known that 4-aminoanthrone (III) can be obtained from the carboxylic acid (II) by cyclization with the aid of sulphuric acid (compare German Patent 593,417 and equation 3):

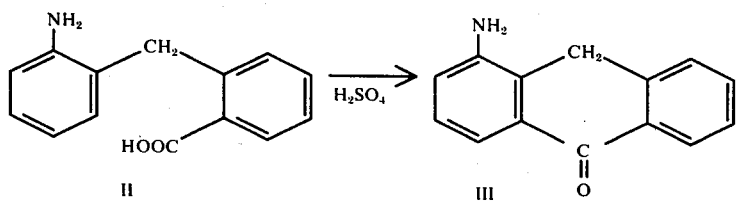

Equation 3

No data is available on the yield of the reaction, on the amount of sulphuric acid required or on the amount of water required to cause the reaction product to separate out. Neither is it known whether the sulphuric acid is obtained after the reaction in a form which is suitable for recovery and reuse.

German Patent 593,417 also contains a note that 1-aminoanthraquinone (IV) can be obtained from an alkaline solution of 4-aminoanthrone (III) by letting it stand in air or by adding an oxidizing agent (see equation 4):

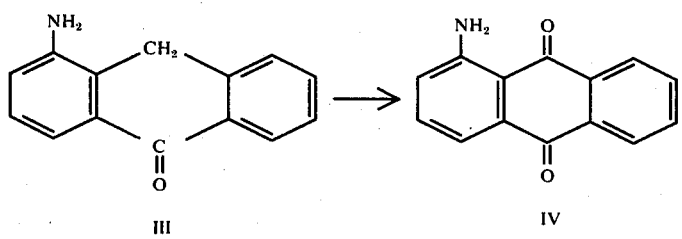

Equation 4

If an alkaline solution is oxidized with air in accordance with these instructions however, 1-aminoanthraquinone is obtained in only 39% yield (see Example 9). In addition, a considerable amount of 4,4'-diamino-dihydro-dianthrone is produced.

The data available from the published literature are scanty and in no way show what conditions have to be selected and what auxiliaries are used with advantage to obtain good yields of 1-aminoanthraquinone. According to the information hitherto available concerning the individual process stages, the method is so involved and the results, where stated at all, are so unfavorable, that there is prejudice against combining these process steps in order to prepare large quantities of 1-amino-anthraquinone.

According to the present invention, there is provided a process for the preparation of 1-aminoanthraquinone comprising the steps of (a) reacting o-chloromethylphenylisocyanate with at least an equivalent amount of benzene in anhydrous hydrofluoric acid at a temperature of about −10° to 200° C to from the lactam of 2-amino-diphenylmethane-2'-carboxylic acid which may then be isolated by removing the unconverted benzene and the hydrofluoric acid, (b) saponifying the lactam of 2-amino-diphenylmethane-2'-carboxylic acid with aqueous alkali at a temperature above about 100° C to form a 2-amino-diphenylmethane-2'-carboxylic acid, which may then be isolated and dried, (c) converting the 2-amino-diphenylmethane-2'-carboxylic acid, in the presence of acid condensation agents, into 4-aminoanthrone, which may be separated out by adding water and/or ice and (d) converting the 4-aminoanthrone into 1-aminoanthraquinone, by addition of oxidizing agents, if appropriate with addition of a solvent, in an acid or alkaline medium.

The discovery that the combination of the process steps of the invention enables large amounts of 1-aminoanthraquinone to be prepared from easily accessible o-chloromethylphenylisocyanate and benzene must be described as distinctly surprising.

With regard to the o-chloromethylphenylisocyanate required as the starting material, it is to be noted that arylisocyanates chlorinated in the side chain are known compounds and can be prepared for example, by the process described in Houben-Weyl, Methoden der Organischen Chemie (Methods of Organic Chemistry), 4th edition, volume V/3, page 746 (1968). With regard to the preparation of o-chloromethylphenylisocydnate required as the starting material for the process according to the invention, reference should also be made to Example 1.

Process step (a) is in general carried out by reacting o-chloromethylphenylisocyanate with at least an equimolecular amount, and preferably about 2 to 5 times the equimolecular amount, of benzene in anhydrous hydrofluoric acid. Commercially available anhydrous hydrofluoric acid containing at least about 99% of hydrogen fluoride can be used as the anhydrous hydrofluoric acid. Hydrofluoric acid is preferably used in about a 6-fold to 10-fold molar excess since it serves both as the catalyst and as the solvent. The reaction is in general carried out in the temperature range of −10° to 200° C. Preferably, the reaction is carried out in two steps, first in the temperature range of about 0°–20° and then in the temperature range of about 40°–120° C. The reaction takes place practically quantitatively. The unconverted benzene and hydrofluoric acid can be removed, for example, by distillation and be reused after adjusting to the correct ratio. The lactam of 2-amino-diphenylmethane-2'-carboxylic acid which remains after removing benzene and hydrofluoric acid is practically pure and can be processed further without additional purification.

Process step (a) can also be carried out by first taking anhydrous hydrofluoric acid, injecting inert gas, for example nitrogen, up to a pressure in the range of about 0.5 to 5 bars, and then heating the hydrofluoric acid. A solution of o-chloromethylphenylisocyanate in benzene is introduced under pressure into the heated hydrofluoric acid. The hydrogen chloride produced is released through a pressure-retaining valve. After completion of the reaction, and after cooling the reaction mixture, the excess hydrofluoric acid is removed, for example by distillation. After adding a dilute solution of an alkaline agent to the benzene solution which remains, the lactam of 1-amino-diphenylmethane- 2'-carboxylic acid can be isolated by filtration. If desired, an additional quantity of the lactam of 2-amino- diphenylmethane-2'-carboxylic acid can be obtained by separating off the aqueous phase and concentrating the benzene phase. Le A 15 805

Process step (b) is in general carried out by treating the lactam of 2-amino-diphenylmethane-2'-carboxylic acid with an alkaline aqueous solution. The alkaline aqueous solution can be prepared, for example, by dissolving the hydroxides and/or oxides of the alkali metals and/or alkaline earth metals in water. Aqueous sodium hydroxide solution is used preferentially. The alkalis are in general employed in 2 to 4.5 times the stoichiometric amount, preferably in about 2 to 2.5 times the stoichiometric amount, based on the lactam of 2-aminodiphenylmethane- 2'-carboxylic acid. It is also possible to employ the alkalis in about 1 to 2 times the stoichiometric amount or in about 1.3 to 1.8 times the stoichiometric amount based on the lactam. The temperature can vary within wide limits but should be above about 100°C. Preferably, the reaction is carried out in the temperature range of about 150°–200°C. To isolate the 2-amino-diphenylmethane- 2'-carboxylic acid, the clear aqueous solution can be adjusted to a pH value near the isoelectric point, preferably to a pH value in the range of about 4.5 to 5.5, by addition of acids, for example hydrochloric acid or sulphuric acid, whereupon 2-amino-diphenylmethane-2'-carboxylic acid precipitates. The 2-amino-diphenylmethane-2'-carboxylic acid can also be isolated in the form of the Na salt which can be caused to separate out from the alkaline saponification solution by adding sodium chloride and/or by cooling. The sulphate or hydrochloride, which precipitates on acidifying the cold saponification solution, can also be used for the isolaton process. The 2-amino-diphenylmethane-2'-carboxylic acid can, for example, be dried in vacuo. Higher temperatures should be avoided during drying since there is otherwise the danger of re-formation of the lactam.

It is a particular advantage of the process according to the invention that the process steps (a) and (b) can be carried out in the same reaction vessel.

Process step (c) is in general carried out by treating 2-amino-diphenylmethane-2'-carboxylic acid with acid condensation agents. Examples of acid condensaton agents are sulphuric acid, chlorosulphonic acid, fluorosulphonic acid, methanesulphonic acid, trifluoromethanesulphonic acid, phosphoric acid, polyphosphoric acid, hydrofluoric acid, aluminum chloride, zinc chloride, tin-(IV) chloride, titanium-(IV) chloride, phosphorus oxychloride, acetic acid together with phosphorus pentoxide, thionyl chloride and benzoyl chloride. Preferably, concentrated sulphuric acid is used as the acid condensation agent. The concentration of the sulphuric acid can be, for example, about 85–105%. The use of 100% strength sulphuric acid is very particularly preferred. Where sulphuric acid is used as the acid condensation agent, it is in general employed in an amount by weight which is about 4 to 10 times, preferably about 5 to 8 times, the amount by weight of the carboxylic acid. To isolate the 4-aminoanthrone, water, either liquid or as ice, is added to the reaction product.

Where sulphuric acid is used as the acid condensation agent, preferably sufficient water is added that after the addition the sulphuric acid concentration lies in the range of about 20 to 75%, preferably about 40 to 70%. In that case it is possible to recover and re-use the sulphuric acid. The 4-aminoanthrone then separates out as the sulphate in the form of a paste containing sulphuric acid, which is suitable for direct further processing. The reaction is generally carried out in the temperature range of about 20–80°C, preferably about 40°–60°C.

Process step (d), which comprises the oxidation of 4-aminoanthrone to 1-aminoanthraquinone, can be carried out in either an acid or an alkaline medium. Preferably, an alkaline medium is used. Examples of alkaline agents which can be used are the hydroxides, oxides, carbonates, bicarbonates, borates, aluminates, silicates and phosphates of the alkali metals and/or alkaline earth metals, as well as ammonia and its alkyl-substituted products, for example methylamine, dimethylamine, trimethylamine and their homologues. The amount of the alkaline agent can vary within wide limits, for example between about 0.05 to 10, preferably between about 0.1 and 1, times the stoichiometric amount of 4-aminoanthrone employed. Examples of oxidizing agents which can be used are air, oxygen, hydrogen peroxide, perborates, peroxydisulphates, peroxymonosulphates, peroxydiphosphates, peroxymonophosphates, peroxymolybdates, peroxytungstates, peroxytitanyl sulphates, peroxytitanates, nitric acid, chlorine and sulfurtrioxide. The oxidizing agent is in general employed in equivalent amount. It is also possible to use an excess of oxidizing agent. Preferably, hydrogen peroxide is used in concentrations of about 3 to 30%, in which case the reaction is in general carried out at between about 0° and 100°C, preferably between about 40° and 80°C, and especially between about 60° and 80°C.

The oxidation can advantageously be carried out in the presence of a solvent so that it takes place in an organic/ aqueous phase. Suitable solvents for the purpose are ketones, alcohols, aromatic hydrocarbons and halogen- substituted aromatic and aliphatic hydrocarbons. The following may be mentioned as examples: acetone, methyl ethyl ketone, diethyl ketone, methyl propyl ketone, methyl butyl ketone, cyclohexanone, methyl isopropyl ketone, methyl isobutyl ketone, methanol, ethanol, isopropanol, butanol, toluene, benzene, xylene, chlorobenzene, chloroform, methylene chloride and carbon tetrachloride. In particular, ketones are employed preferentially, examples being methyl ethyl ketone and methyl isopropyl ketone.

The process according to the invention can be illustrated by equation 5.

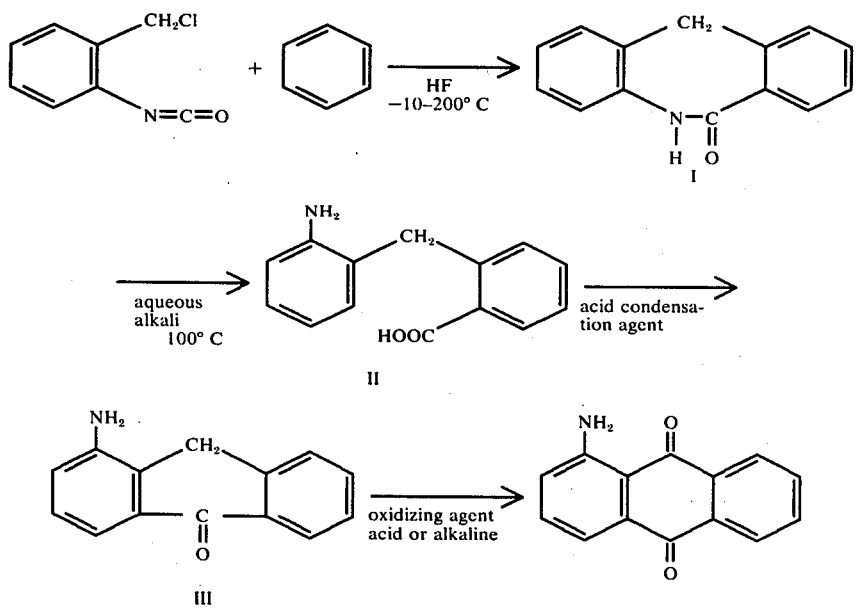

Equation 5

In a particularly preferred embodiment of the invention, the procedure adopted is as follows:

Anhydrous hydrofluoric acid is initially introduced into a stainless steel autoclave which is fitted with a stirring device, a pressure-resistant reflux condenser followed by an adjustable relief valve, and a heating and cooling device. A solution of o-chloromethylphenylisocyanate in benzene is run in, while stirring, at a temperature of about -10° to 10°C. Approximately 2 to 5 moles of benzene and approximately 6 to 10 moles of anhydrous hydrofluoric acid are used per mole of o-chloromethylphenylisocyanate. After completion of the addition, the temperature of the reaction mixture is allowed to rise to about 10°–20°C, whereupon a vigorous evolution of hydrogen chloride commences. When the evolution of hydrogen chloride has subsided, the relief valve is closed and a pressure of about 4 to 10 bars is maintained; if appropriate, this pressure can also be applied by means of an inert gas, for example $CO_2$ or $N_2$. The reaction mixture is heated to a temperature in the range from about 40° to 100°C and is kept at this temperature for between about half an hour and two hours. It is then cooled to about 15°–19°C and the autoclave is released. Excess benzene and hydrogen fluoride are distilled off and re-used if appropriate. The solid which is left consists of practically pure lactam of 2-amino- diphenylmethane-2'-carboxylic acid and has a melting point of 196° to 199°C. The precipitate is next stirred with water, and sodium hydroxide, in the solid form or in the form of a concentrated solution, is then added in about 2 to 2.5 times the equimolar amount, relative to the lactam. The mixture is warmed for some hours to a temperature in the range of about 150° to 200°C. After cooling to room temperature, the clear solution obtained is adjusted with sulphuric acid to a pH value in the range of the isoelectric point, whereupon 2-amino-diphenylmethane-2'-carboxylic acid separates out. The precipitate is filtered off and dried in vacuo at not more than about 50°C. The dried precipitate is introduced, while stirring, into about a 5-fold to 8-fold amount of about 85 to 110% strength sulphuric acid (based on the weight of the carboxylic acid). During the addition, and for about 20 to 120 minutes after, the temperature is kept in the range from about 20 to 80°, preferably in the range from about 40° to 60°C. The reaction mixture is then poured onto ice, taking care that the concentration of sulphuric acid in the resulting solution is at least about 20%. Under these circumstances, the sulphuric acid can be reconcentrated economically and be re-used in any desired processes. The 4-aminoanthrone precipitates and is obtained, after filtration, in the form of a paste containing sulphuric acid. The paste containing sulphuric acid is suspended in water and sufficient concentrated sodium hydroxide solution is added to give a suspension which reacts neutral. The product is filtered off, the resulting moist paste is suspended in water, an alkaline agent, for example sodium hydroxide solution or sodium silicate is added and the resulting mixture is brought to a temperature between about 40° and 80°C, while adding an at least equivalent amount of hydrogen peroxide, and stirring. If necessary, the mixture can be stirred for some hours longer, at an elevated temperature, to complete the reaction. The 1-aminoanthraquinone which has precipitated can be obtained in a pure form by filtration, washing with water to remove the adhering alkali solution, and subsequent drying.

The process according to the invention has the following advantages over the known processes for the preparation of 1-aminoanthraquinone: as a result of the use of new starting products and as a result of the different course of the reaction, no isomers are formed, while isomers are formed, for example, when 1-aminoanthraquinone is prepared via anthraquinone-1-sulphonic acid or via nitroanthraquinone. Furthermore, the process according to the invention can be carried out in such a way that most of the auxiliaries can be recovered and re-used.

1-Aminoanthraquinone is a central intermediate product which can be used for the preparation of a range of anthraquinone compounds which in turn can be used for the preparation of a large number of dyes for a great variety of fields of use (compare Ullmann, Enzyklopaedie der technischen Chemie (Encyclopaedia of Industrial Chemistry), volume 3, page 730, 3rd edition).

The invention will be further described in the following illustrative examples.

EXAMPLE 1 (preparation of o-chloromethylphenylisocyanate)

950 g (7.14 moles) of 2-methyl-phenyl-isocyanate of boiling point 70°C/10 mm Hg ($n_D^{20}$: 1.5360) are initially introduced into a three-necked flask fitted with a stirrer, reflux condenser and gas inlet frit. A total of 480 g (6.75 moles) of chlorine are introduced at about 100°C while irradiating the mixture with UV light. Thereafter excess chlorine, and hydrogen chloride formed, are flushed out for about one hour at about 120°–130°C by passing nitrogen through the reaction mixture, and the latter is then worked up by fractional distillation. 607 g (3.63 moles) of 2-chloromethyl-phenylisocyanate are obtained in the boiling range of 112°–114°C/12 mm Hg; $n_D^{20}$: 1.5670.

EXAMPLE 2 (process according to the invention)

The condensation with anhydrous hydrofluoric acid described below is carried out in a stainless steel autoclave which is fitted with a stirring device, pressure-resistant reflux condenser followed by an adjustable relief valve, and cooling and heating devices. 100 ml of anhydrous hydrofluoric acid are first introduced into this autoclave. A solution of 85 g of o-chloromethyl-phenylisocyanate in 200 ml of anhydrous benzene is allowed to run in at a temperature of about 0°C, while stirring. Evolution of hydrogen chloride commences. The mixture is stirred for about 1–2 hours longer at 10°–15°C, the autoclave is then sealed, a protective pressure of 10 atmospheres gauge $N_2$ is set up in the autoclave and the latter is heated to 100°C internal temperature. When the pressure remains constant, the autoclave is cooled and released. The mixture is then distilled under normal pressure until the temperature at which material passes over reaches about 50°C. An azeotrope of benzene and HF distils off. A clear solution is now left in the autoclave, and is run into 170 ml of ice water. The precipitate is filtered off at a temperature above 6°C. The benzene phase is separated from the filtrate. The filter cake, while still moist, is stirred vigorously with about 330–500 ml of 5% strength KOH and is then filtered off, washed with water until neutral and dried. 100 g of 2- amino-diphenylmethane-2'-carboxylic acid lactam are thus obtained. Melting point: 193°–196°C. (A sample recrystallized once from toluene has a melting point of 199°–200°C).

The 2-amino-diphenylmethane-2'-carboxylic acid lactam thus obtained is stirred with 500 ml of water, sufficient sodium hydroxide solution is then added to produce a neutral suspension and thereafter 60 g of sodium hydroxide or the corresponding amount of a concentrated sodium hydroxide solution are added. The mixture is warmed to 180°C for 6 hours. After cooling to room temperature, the resulting clear solution is brought to pH 5 with 30% strength sulphuric acid, whereupon 2-amino-diphenylmethane-2'-carboxylic acid separates out in the form of colorless crystals. The mixture is filtered and the residue is dried at 40°C in a vacuum drying cabinet. 108 g (94% of theory, including both stages) of 2-amino-diphenylmethane-2'-carboxylic acid of melting point 124°–128°C are obtained. 108 g of the 2-amino-diphenylmethane-2'-carboxylic acid thus obtained are introduced into 800 g of 100% strength sulphuric acid while stirring and keeping the temperature below 40°C. The temperature is then kept for half an hour at 45°C, after which the reaction mixture is immediately poured out onto 1,200 g of ice, whereupon the sulphate of 4-aminoanthrone precipitates in greenish-yellow crystals. After brief stirring in an ice bath, the product is filtered off. 200 g of a paste containing sulphuric acid are obtained. (The yield was determined in a parallel experiment wherein the paste, containing sulphuric acid, which was obtained was stirred in 500 ml of ice water, brought to pH 7 by adding sodium hydroxide solution and then filtered off. After drying, 95 g (95.5% of theory) of 4-aminoanthrone of melting point 164° to 168°C were obtained.)

200 g of the paste containing sulphuric acid, which is obtained as described above, are suspended in 1 l of water and sufficient concentrated sodium hydroxide solution is added to give a neutral suspension in water. The product is filtered off and resuspended in 1 l of water, 150 ml of 2 N sodium hydroxide solution are then added and the mixture is warmed to 60°C. At this temperature, 90 ml of a 30% strength aqueous hydrogen peroxide solution are added dropwise in the course of one hour. After stirring for 4 hours at 60°C, filtering off the hot solution, eluting the alkali, still adhering to the precipitate, with water, and drying, 95 g of 1-aminoanthraquinone of 91% purity (85% of theory) are obtained.

EXAMPLE 3: (variation in the preparation of the lactam of 2- amino-diphenylmethane-2'-carboxylic acid)

75 ml (3.75 moles) of anhydrous hydrofluoric acid are introduced into the autoclave described in Example 2. The autoclave is sealed, nitrogen is injected up to a pressure of 3 bars and the mixture is then heated to about 40°C. At this temperature, a solution of 85 g (0.51 mole) of 2-chloromethylphenylisocyanate in 160 g (2.05 moles) of benzene is forced in, over the course of 35 minutes, by means of a metering pump. The hydrogen chloride produced is released at 4.5 bars via the relief valve. The temperature is maintained for a further 2 hours, while stirring vigorously. After cooling, the pressure is released, the hydrogen fluoride is stripped off under reduced pressure, the benzene solution which is left is extracted by shaking once with 1,460 ml of aqueous 5% strength by weight potassium hydroxide solution and the reaction product which hereupon precipitates is filtered off. 70 g (66% of theory) of 2-amino-diphenylmethane-2'- carboxylic acid lactam of melting point 191°–195°C are obtained. After separating off the aqueous phase, and concentrating the benzene phase, a further 10 g of crude product are obtained.

EXAMPLE 4 (variation in the preparation of 2-amino-diphenylmethane- 2'-carboxylic acid)

The saponification of the lactam of 2-amino-diphenylmethane- 2'-carboxylic acid is carried out in accordance with Example 2, except that the mixture is warmed to 160°C for 12 hours. The yield of 1-aminodiphenylmethane-2'- carboxylic acid is practically the same as in Example 2.

EXAMPLE 5 (variation in the preparation of 4-aminoanthrone)

108 g of the 2-amino-diphenylmethane-2'-carboxylic acid obtained according to Example 2 or 4 are introduced, while stirring, into 540 g of 100% strength sulphuric acid, while keeping the temperature below 40°C. Thereafter the mixture is warmed to 40°C for one hour and then to 50 °C for a further hour. After cooling in an ice bath, the yellowish-green sulphuric acid solution is diluted by dropwise addition of 360 ml of water, whereupon the sulphate of 4- aminoanthrone separates out in the cold. After filtering off, and suspending the residue in 1 l of water, sufficient concentrated sodium hydroxide solution is added to give a neutral suspension. After brief stirring, the product is again filtered off and dried. 85.5 g (86% of theory) of 4-aminoanthrone of melting point 158 ° to 161°C are obtained.

EXAMPLE 6 (variation in the preparation of 4-aminoanthrone)

108 g of the 2-amino-diphenylmethane-2'-carboxylic acid obtained according to Example 2 or 4 are introduced into 700 g of 100% strength sulphuric acid at a temperature below 50°C. Thereafter the mixture is stirred for half an hour at 45°C and the yellowish-green solution is then poured out onto 700 g of ice. The sulphate of 4-aminoanthrone precipitates in yellowish-green crystals. After cooling in an ice bath to 0°–5°C, the mixture is filtered, the residue is stirred with 1 l of water, the resulting suspension neutralized with sodium hydroxide solution and the product again filtered off. After drying in a vacuum drying cabinet at 80°C, 90 g (90.5% of theory) of 4-aminoanthrone of melting point 158° to 161°C are obtained.

EXAMPLE 7 (variation in the oxidation of 4-aminoanthrone to 1-aminoanthraquinone)

200 g of a paste which contains 95 g of 4-aminoanthrone and also contains sulphuric acid, and which is obtained in accordance with the instructions of Example 2, are suspended in 1 l of water and neutralized with concentrated sodium hydroxide solution, and the 4-aminoanthrone is filtered off. It is equally possible to start from the corresponding amount of 4-aminoanthrone which has been obtained according to Example 5 or 6. The 4-aminoanthrone is now stirred into 1 l of water, 150 ml of potassium waterglass ($d = 1.25$) are added, the mixture is warmed to 60°C and 500 ml of 6% strength hydrogen peroxide solution are added dropwise in the course of 2 hours. This causes the color of the suspension to change from yellow to red. The mixture is stirred for a further 3 hours and is filtered, and the residue is washed until neutral. After drying, 100 g of 1-aminoanthraquinone of 90% purity (89% of theory) are obtained.

EXAMPLE 8 (variation in the oxidation of 4-aminoanthrone to 1-aminoanthraquinone)

The procedure followed is as described in Example 7 except that 15 g of trisodium phosphate are added, the mixture is warmed to 60°C and 500 ml of a 6% strength hydrogen peroxide solution are added dropwise in the course of 30 minutes. Working up takes place as described in Example 7. 98 g of 1-aminoanthraquinone of 86% purity (83% of theory) are obtained.

EXAMPLE 9 (comparison example relating to the oxidation of 4-aminoanthrone to 1-aminoanthraquinone in accordance with German Patent 593,417).

6.3 g of 4-aminoanthrone are dissolved in 100 ml of hot 1 N KOH. Air is then passed through the solution at 80°C until the yellow exudation from a spot test has disappeared. After filtering off and washing until neutral, 4.5 g of product containing 58.2% of 1-aminoanthraquinone (39% yield) are obtained. On boiling with toluene, which dissolves the 1-aminoanthraquinone, a yellow residue is obtained which according to analysis, NMR-spectrum, IR-spectrum, mass spectrum and molecular weight determination is 4, 4'-diamino-dihydrodianthrone (melting point: 251°–253°C).

EXAMPLE 10

Saponification to 2-amino-diphenylmethane-2'-carboxylic acid 107 g of lactam (0.513 mole) are warmed in a mixture of 70 ml of concentrated sodium hydroxide solution ($d = 1.48$) and 630 ml of water for 8 hours to 180°C in a refined steel autoclave. The excess pressure hereupon built up is about 10 atmospheres gauge. After cooling, a clear solution is obtained which at times has to be clarified because of a trace of black impurity, probably originating from the autoclave material. The filtrate amounts to 750 ml and according to determination has a nitrite value of 35.2 g of sodium nitrite = 100 %. The clear solution is brought to pH 5 by dropwise addition of about 90 ml of 50% strength sulphuric acid at 15°–20°C, whereupon the colorless betaine of the aminocarboxylic acid precipitates. The mixture is stirred further until the pH value remains constant and is then filtered. The precipitate on the filter is twice covered with 100 ml of water. The filtrate measures 930 ml and has according to determination a nitrite value of 0.3 g of sodium nitrite = 0.9 %. The paste weighs 200 g. After drying in a vacuum drying cabinet at 50°C, 115 g (99% yield) are obtained. Melting point 124°–125°C.

Cyclization to give 4-aminoanthrone 115 g of 2-amino-diphenylmethane-2'-carboxylic acid (0.507 mole) are introduced into 350 ml of monohydrate while ensuring, through slight cooling with a water bath, that the temperature does not rise above 40°C. The mixture is then warmed to 40°C for three hours, whereupon a clear greenishyellow solution results. This is cooled to room temperature and the melt is poured out onto 650 g of ice, whereupon the sulphate of 4-aminoanthrone separates out in the form of greenish-yellow crystals. The mixture is left to stand for some hours in an ice bath and is filtered. The filtrate measures 820 ml and has according to determination a nitrite value of 1.1 g of sodium nitrite = 3.2 %. The paste is stirred into 500 ml of water and brought to pH 7 with 234 ml of sodium hydroxide solution (1 part by volume of concentrated NaOH/1 part by volume of water) in a nitrogen atmosphere. 3 g of sodium bicarbonate are then added and the mixture is warmed to 60°C for 1 hour. After warming for one hour, the pH value should be between 7.5 and 8.5. The mixture is filtered and the residue is twice covered with 150 ml of water at a time. The paste weighs 250 g. The filtrate measures 1,200 ml and has according to determination a nitrite value of 2.3 g of sodium nitrite.

Oxidation to give 1-aminoanthraquinone

The moist paste of 4-aminoanthrone is introduced into 300 ml of water and warmed to 60°C under nitrogen. The pH is checked every ¼ of an hour and should lie in the range between 7.5 and 8.5. 75 ml of potassium waterglass ($d = 1.25$) are then added, whereupon a pH of 11 results. 375 ml of $H_2O_2$ solution are then added dropwise in the course of 2.5 hours, the solution being prepared by diluting 200 ml of 35% strength hydrogen peroxide ($d = 1.135$) to 1.0 liter. The mixture is warmed to 70°C and kept at this temperature for one hour. 500 ml of the azeotrope of methyl ethyl ketone (88%) and water (12%) which boils at 73.4°C, are then added and the mixture is heated to the boil for 10 hours (temperature 74°C). It is then cooled to 20°C, stirred for 1 hour at room temperature and then filtered. The residue is covered twice with 150 ml of water at a time, to remove the adhering methyl ethyl ketone. The azeotrope (boiling point 73°C) is recovered almost quantitatively from the combined filtrates by distillation. 4 g of a solid substance which contains about 50% of 1-aminoanthraquinone are isolated from the distillation residue. To remove adhering silica the moist paste of the 1-aminoanthraquinone, in 500 ml of water and 60 ml of concentrated sodium hydroxide solution ($d = 1.48$) must be subjected to incipient distillation for ~15 minutes. To avoid objectionable foaming during this operation, 5 drops of anti-foam agent are added. The product is filtered off hot, and the adhering sodium hydroxide solution is eluted with a little hot water. The paste weighs 140 g. It is dried at 70°C. 91 g are obtained.

| | | |
|---|---|---|
| 1-Aminoanthraquinone | 94.5 – | 95.5% |
| 4-Aminoanthrone | 1.0 – | 2.0% |
| 4,4-Diamino-dihydro-dianthrone | 0.0 – | 0.5% |
| Ash (silica) | 0.05 – | 0.3% |
| THF - insolubles | | 0.3% |
| Melting point 250–254° C. | | |

EXAMPLE 11: (variation in the preparation of 2-amino-diphenylmethane- 2'-carboxylic acid)

18 g sodium hydroxide or the corresponding amount of concentrated sodium hydroxide solution and 100 ml water are added to 64 g of 2-amino-diphenylmethane-2'-carboxylic acid lactam in an autoclave. The mixture is warmed to 180°C for 5 hours. After cooling to room temperature a pulp of crystals is obtained which dissolves after dissolution with water. This solution is brought to pH 5 with 50 % strength sulphuric acid at room temperature, whereupon the betaine of 2-amino-diphenylmethane- 2'-carboxylic acid separates out in the form of colorless crystals. The mixture is filtered and the residue is dried at 40°C in a vacuum drying cabinet. The yield is 68.8 g (99 % of theory). The melting point of the obtained product is 124° – 128°C.

It will be appreciated that the instant specification and examples are set forth by way of illustration and not limitation, and that various modifications and changes may be made without departing from the spirit and scope of the present invention.

What is claimed is:

1. A process for preparing 1-aminoanthraquinone, comprising the steps of:
   a. reacting o-chloromethylphenylisocyanate with at least an equivalent amount of benzene in anhydrous hydrofluoric acid at a temperature of about −10° to 200°C to form the lactam of 2-amino-diphenylmethane-2'-carboxylic acid.
   b. saponifying the lactam of 2-amino-diphenylmethane- 2'-carboxylic acid with aqueous alkali at a temperature above about 100°C to form the 2-amino- diphenylmethane-2'-carboxylic acid,
   c. contacting the 2-amino-diphenylmethane-2'- carboxylic acid with an acid condensation agent, thereby to convert the carboxylic acid to 4-aminoanthrone, and
   d. contacting the 4-aminoanthrone with an oxidizing agent in an acid or alkaline medium, thereby to convert the aminoanthrone to 1-aminoanthraquinone.

2. A process according to claim 1 wherein (a) is carried out in two stages, the first stage being conducted at a temperature of about 0° to 20°C and the second stage being conducted at a temperature of about 40° to 120°C.

3. A process according to claim 1, wherein in a there are employed about 2 to 5 moles of benzene and about 6 to 10 moles of hydrofluoric acid per mole of o-chloromethylphenylisocyanate.

4. A process according to claim 1, wherein sodium hydroxide is the aqueous alkali in b.

5. A process according to claim 4, wherein about 1 to 4.5 moles of sodium hydroxide are employed per mole of lactam.

6. A process according to claim 5, wherein about 1.3 to 2.5 moles of sodium hydroxide are employed per mole of lactam.

7. A process according to claim 1, wherein b is carried out at a temperature of about 150° to 200°C.

8. A process according to claim 1, wherein the acid condensation agent in c is sulphuric acid.

9. A process according to claim 8, wherein 100% sulphuric acid is used in about 4 to 10 times the weight of 2-amino-diphenyl-methane-2'-carboxylic acid.

10. A process according to claim 9, wherein 100% sulphuric acid is used in about 5 to 8 times the weight of the carboxylic acid.

11. A process according to claim 1, wherein c is carried out at a temperature of about 20° to 80°C.

12. A process according to claim 11, wherein c is carried out at a temperature of about 40° to 60°C.

13. A process according to claim 8, wherein sulphuric acid is employed in an initial concentration of at least about 85% and after said condensation sufficient water is added to give a sulphuric acid concentration of about 20 to 75%, the aminoanthrone thereby separating out.

14. A process according to claim 13, wherein sufficient water is added to give a sulphuric acid concentration of about 40 to 70%.

15. A process acording to claim 1, wherein hydrogen peroxide is the oxidizing agent in d.

16. A process according to claim 1, wherein d is carried out at a temperature of about 40° to 80°C.

17. A process according to claim 16, wherein d is carried out at a temperature of about 60° to 80°C.

18. A process according to claim 1, wherein about 0.05 to 10 moles of an alkaline agent are present per mole of 4-amino-anthrone to be oxidized.

19. A process according to claim 18, wherein the alkaline agent is a silicate.

20. A process according to claim 19, wherein the silicate is sodium waterglass or potassium waterglass.

21. A process according to claim 1, wherein $d$ is carried out in the presence of a solvent.

22. A process according to claim 21, wherein the solvent comprises at least one ketone, alcohol, aromatic hydrocarbon, halogenated aromatic hydrocarbon or halogenated aliphatic hydrocarbon.

23. A process according to claim 21, wherein the solvent comprises methyl ethyl ketone.

24. A process according to claim 21, wherein the solvent comprises methyl isopropyl ketone.

* * * * *

UNITED STATES PATENT AND TRADEMARK OFFICE
CERTIFICATE OF CORRECTION

PATENT NO. : 4,006,170  Page 1 of 2
DATED : February 1, 1977
INVENTOR(S) : Horst Jager, et al.

It is certified that error appears in the above–identified patent and that said Letters Patent are hereby corrected as shown below:

| | |
|---|---|
| Col. 1, line 31 | cancel "Enzyklopadie" and substitute -- Enzyklopädie -- |
| Col. 2, lines 14-15 | cancel "dipehnylmethane" and substitute -- diphenylmethane -- |
| Col. 2, line 40 | cancel "preparaton" and substitute -- preparation -- |
| Col. 4, line 54 | cancel "phenylisocydnate" and substitute -- phenylisocyanate -- |
| Col. 5, line 29 | delete "Le A 15805" |
| Col. 6, line 1 | cancel "condensaton" and substitute -- condensation -- |
| Col. 7, equation 5 | in second part of equation, before "100°C" insert -- $\geqslant$ -- |
| Col. 9, line 6 | cancel "Enzyklopadie" and substitute -- Enzyklopädie -- |

UNITED STATES PATENT AND TRADEMARK OFFICE
CERTIFICATE OF CORRECTION

PATENT NO. : 4,006,170
DATED : February 1, 1977
INVENTOR(S) : Horst Jager, et al.

It is certified that error appears in the above-identified patent and that said Letters Patent are hereby corrected as shown below:

Col. 12, line 51      cancel "greenishyellow" and substitute -- greenish-yellow --

Claim 3
   Col. 14, line 25      cancel "athere" and substitute -- (a) there --

Signed and Sealed this

Twenty-seventh Day of September 1977

[SEAL]

Attest:

RUTH C. MASON
*Attesting Officer*

LUTRELLE F. PARKER
*Acting Commissioner of Patents and Trademarks*